US00PP13332P3

(12) United States Plant Patent
Zary

(10) Patent No.: US PP13,332 P3
(45) Date of Patent: Dec. 10, 2002

(54) HYBRID TEA ROSE PLANT NAMED 'JACERGMA'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/779,326

(22) Filed: Feb. 7, 2001

(65) Prior Publication Data

US 2002/0108155 P1 Aug. 8, 2002

(51) Int. Cl.[7] ..... A01H 5/00

(52) U.S. Cl. ..... Plt./140

(58) Field of Search ..... Plt./140, 130, 139

*Primary Examiner*—Bruce R. Campell
*Assistant Examiner*—June Hwu
(74) *Attorney, Agent, or Firm*—Klarquist Sparkman, LLP

(57) ABSTRACT

A hybrid tea rose plant having vigorous upright growth; dark green, leathery foliage; and bright red, high centered blooms that are long lasting as cut flowers.

1 Drawing Sheet

LATIN NAME OF GENUS AND SPECIES

*Rosa hybrida.*

VARIETY DENOMINATION

'JACergma'.

SUMMARY OF THE INVENTION

The present invention relates to a new and distinct variety of rose plant of the hybrid tea class which was originated by me by crossing the variety 'POULman', U.S. Plant Pat. No. 6,264, with the variety 'JACbor'. U.S. Plant Pat. No. 6,668.

BACKGROUND OF THE INVENTION

The primary objective of this breeding was to produce a new rose variety having the bright red flower, fairly compact growth and dark green leathery foliage of the female parent combined with the well formed flowers, continuous bloom and vigorous upright growth of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Bright red flowers;
2. Dark green, leathery foliage;
3. Vigorous, upright growth;
4. Long lasting cut flowers; and
5. High centered blooms.

Asexual reproduction of this new variety by budding on 'Dr. Huey' (unpatented) understock, as performed at Wasco, Calif., shows that the foregoing and all other characteristics and distinctions come true to form and are established and transmitted through succeeding propagations.

COMPARISON WITH PARENTS

The female parent, 'POULman', has larger flowers with more petals than JACergma. The male parent, 'JACbor', has larger flowers of orange color but shorter vase life.

COMPARISON WITH SIMILAR VARIETY

'JACergma' differs from 'JAColber' in that 'JACergma' has a more compact plant habit, brighter red flowers on shorter stems and has greater disease resistance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—'POULman'. (U.S. Plant Pat. No. 6,264).
*Pollen parent.*—'JACbor'. (U.S. Plant Pat. No. 6,668).
Classification:
*Botanical.*—*Rosa hybrida.*
*Commercial.*—Hybrid tea.

FLOWER

Observations made from specimens beginning at two years of age grown in a garden environment at Somis, Calif. in February 1999 to November 2000.

Blooming habit: Continuous.
Bud:
*Size.*—1¾ inches long when the petals start to unfurl.

*Form.*—The bud form is long, pointed ovoid.

*Color.*—When sepals first divide, bud color is Red Group 45B. When half blown, the upper sides of the petals are Red Group 45B; and the lower sides of the petals are Red Group 45A.

*Sepals.*—Color: Green Group 138B. Length: ⅜ inch. Width: ¼ inch–5/16 inch. Surface texture: Covered in fine hairs. There are three normally to heavily appendaged sepals. There are two unappendaged sepals with hairy edges.

*Receptacle.*—Color: Green Group 138A. Shape: Funnel. Size: Large, about ½ inch×⅜ inch. Surface: Smooth.

*Peduncle.*—Length: Medium, averaging about 3 inches. Surface: Rough, prickly, and glandular. Color: Yellow-Green Group 146C to Yellow-Green Group 146D with Greyed-Orange Group 176B in areas exposed to bright sunlight. Strength: Stiff, erect.

Bloom:

*Size.*—Medium. Average open size is 4½ inches.

*Borne.*—Singly.

*Stems.*—Strength: Strong. Average length is about 14 to 16 inches.

*Form.*—When first open: High centered. Permanence: Retains its form to the end, outer petals curl back with some quilling.

*Petalage.*—Number of petals under normal conditions: 25 to 30.

*Color.*—The upper sides of the petals are Red Group 45B. The reverse sides of the petals are Red Group 45A. The base of each petal has a small (3/16"×3/16") Yellow-Orange Group 14B color spot on the upper surface. The lower surface color spot is much smaller and is just a point of yellow color at the point of attachment. The major color on the upper side is Red Group 45B.

*Variegations.*—There are occassional White Group 155D streaks on some petals.

*Discoloration.*—The general tonality at the end of the first day: No change. At the end of the third day: No change. No change through day 7 or 8 on plant or day 9 or 10 in a vase.

*Fragrance.*—Slight.

Petals:

*Texture.*—Thick, leathery.

*Shape.*—Round.

*Form.*—Tips slightly recurved, edges slightly quilled.

*Arrangement.*—Imbricated. There are no petaloids in the center.

*Persistence.*—Petals drop off cleanly before drying.

*Lastingness.*—On the plant: Long (about 7–8 days). As a cut flower: Long (about 9–10 days).

Reproductive parts:

*Stamens.*—Number: 180–200. Anthers: Length: 5/16 inch. Color: Yellow-Orange Group 16D. Arrangement: Regular around styles. Filaments: Color: Red Group 45D. Pollen: Color: Yellow-Orange Group 22B.

*Pistils.*—Number: 100–120. Styles: Color: Red Group 46A on upper ¼ to ⅓, the color shading to Yellow-Orange 20D on the lower portion. Length: 1/16 inch. Stigmas: Color: Yellow-Orange Group 20C. Length: 1/64 inch.

*Hips.*—No natural hip set has been observed.

Plant:

*Form.*—Bush.

*Growth.*—Vigorous, upright, branching. At maturity, height is 5 feet, width is 3½ feet after one full season of growth. Number of leaflets on normal mid-stem leaves: 5 or 7.

Foliage:

*Size.*—Large (6 inches long×4 inches wide).

*Quantity.*—Abundant.

*Color.*—New foliage: Upper surfaces: Greyed-Orange Group 176A. Lower surface: Greyed-Orange Group 176A. Old foliage: Upper surface: Green Group 139A. Lower surface: Green Group 137C.

Leaflets:

*Shape.*—Pointed oval. Base: Rounded. Apex: Acute.

*Texture.*—Leathery, glossy.

*Edge.*—Serrated.

*Serration.*—Single, small.

*Petiole rachis.*—Color: Green Group 137C.

*Petiole underside.*—Smooth with an occassional prickle.

*Stipules.*—Medium and serrated (about ½ inch long). Color: Green Group 137C.

*Disease resistance.*—Resistant to mildew and rust, susceptible to blackspot under normal growing conditions.

Wood:

*New wood.*—Color: Near Greyed-Orange Group 176C. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Medium, hooked slightly downward. Length: ¼ inch.

*Color when young.*—Greyed-Purple Group 183B at the base, then near Yellow-Green Group 147C.

*Color when mature.*—Greyed-Yellow Group 162D to Greyed-Orange Group 165A.

Small prickles:

*Quantity.*—On main stalks: Few. On laterals: Few.

*Color: Greyed-Orange Group* 165A to Greyed-Yellow Group 162D (mature).

Winter hardiness: Hardy to Zone 5.

I claim:

1. A new and distinct variety of rose plant of the hybrid tea class plant as herein shown and described, characterized particularly as to novelty by the unique combination of its vigorous, upright growth; dark green, leathery foliage; and bright red, high centered blooms that are long lasting as cut flowers.

* * * * *

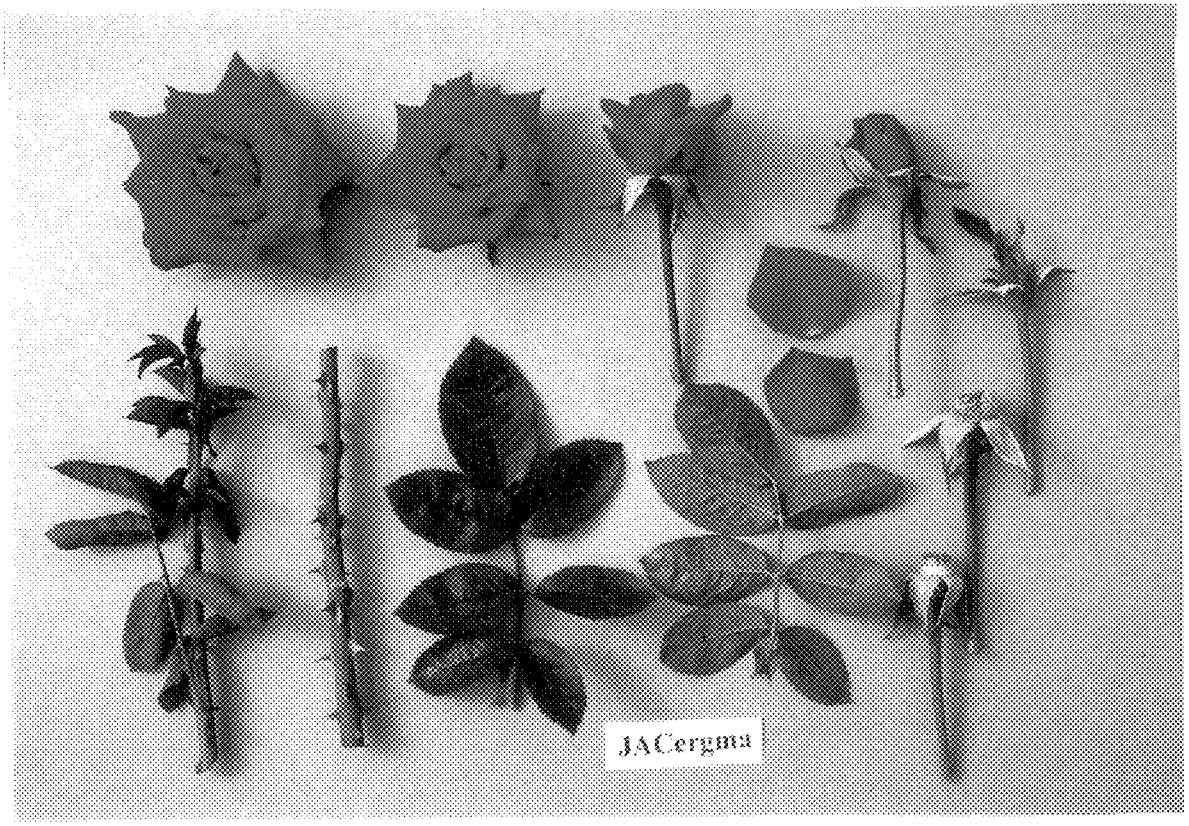
JACergma